(12) United States Patent
Stopek et al.

(10) Patent No.: US 8,353,931 B2
(45) Date of Patent: Jan. 15, 2013

(54) LONG TERM BIOABSORBABLE BARBED SUTURES

(75) Inventors: Joshua Stopek, Wallingford, CT (US); Matthew D. Cohen, Berlin, CT (US)

(73) Assignee: Covidien LP, Mansfield, MA (US)

( * ) Notice: Subject to any disclaimer, the term of this patent is extended or adjusted under 35 U.S.C. 154(b) by 625 days.

(21) Appl. No.: 11/556,002

(22) Filed: Nov. 2, 2006

(65) Prior Publication Data

US 2008/0109036 A1    May 8, 2008

(51) Int. Cl.
*A61B 17/04* (2006.01)

(52) U.S. Cl. ..................................... 606/228

(58) Field of Classification Search ............ 606/228
See application file for complete search history.

(56) References Cited

U.S. PATENT DOCUMENTS

| | | |
|---|---|---|
| 3,123,077 A | 3/1964 | Alcamo |
| 4,024,871 A | 5/1977 | Stephenson |
| 4,429,080 A | 1/1984 | Casey et al. |
| 5,123,913 A | 6/1992 | Wilk et al. |
| 5,133,738 A | 7/1992 | Korthoff et al. |
| 5,226,912 A | 7/1993 | Kaplan et al. |
| 5,236,563 A * | 8/1993 | Loh .................. 204/165 |
| 5,342,376 A | 8/1994 | Ruff |
| 5,451,461 A * | 9/1995 | Broyer ................ 428/364 |
| 5,569,302 A | 10/1996 | Proto et al. |
| 5,683,417 A | 11/1997 | Cooper |
| 5,695,879 A * | 12/1997 | Goldmann et al. .......... 428/364 |
| 5,814,056 A | 9/1998 | Prosst et al. |
| 5,931,855 A | 8/1999 | Buncke |
| 6,063,105 A | 5/2000 | Totakura |
| 6,106,505 A | 8/2000 | Modak et al. |
| 6,143,352 A | 11/2000 | Clark et al. |
| 6,165,202 A | 12/2000 | Kokish et al. |
| 6,203,564 B1 | 3/2001 | Hutton et al. |
| 6,235,869 B1 | 5/2001 | Roby et al. |
| 6,241,747 B1 | 6/2001 | Ruff |
| 6,506,197 B1 | 1/2003 | Rollero et al. |
| 6,562,051 B1 | 5/2003 | Bolduc et al. |
| 6,599,310 B2 | 7/2003 | Leung et al. |
| 6,620,846 B1 | 9/2003 | Jonn et al. |
| 6,773,450 B2 | 8/2004 | Leung et al. |
| 2002/0077661 A1 | 6/2002 | Saadat |
| 2003/0074023 A1 | 4/2003 | Kaplan et al. |
| 2003/0149447 A1 | 8/2003 | Morency et al. |
| 2004/0010275 A1 | 1/2004 | Jacobs et al. |
| 2004/0030354 A1 | 2/2004 | Leung et al. |
| 2004/0060409 A1 | 4/2004 | Leung et al. |
| 2004/0060410 A1 | 4/2004 | Leung et al. |
| 2004/0088003 A1 | 5/2004 | Leung et al. |

(Continued)

FOREIGN PATENT DOCUMENTS

EP    0 499 048 A1    8/1992

(Continued)

OTHER PUBLICATIONS

International Search Report from Application EP 06 01 2688 dated Oct. 9, 2007.

(Continued)

*Primary Examiner* — Corrine M McDermott
*Assistant Examiner* — Christina Lauer

(57) ABSTRACT

Barbed surgical sutures and a method of forming a barbed surgical suture from a degradable material are provided having degradation rates tailored to provide the suture with a desired mass loss profile.

23 Claims, 2 Drawing Sheets

U.S. PATENT DOCUMENTS

| | | | |
|---|---|---|---|
| 2004/0153125 A1* | 8/2004 | Roby | 606/228 |
| 2004/0162580 A1 | 8/2004 | Hain | |
| 2005/0033367 A1 | 2/2005 | Leung et al. | |
| 2005/0267531 A1 | 12/2005 | Ruff et al. | |
| 2006/0111734 A1 | 5/2006 | Kaplan et al. | |
| 2006/0116718 A1 | 6/2006 | Leiboff | |
| 2007/0005110 A1 | 1/2007 | Collier et al. | |
| 2007/0187861 A1 | 8/2007 | Genova | |
| 2009/0105753 A1* | 4/2009 | Greenhalgh et al. | 606/228 |

FOREIGN PATENT DOCUMENTS

| | | |
|---|---|---|
| EP | 0 632 999 A | 1/1995 |
| EP | 0 647 452 A1 | 4/1995 |
| EP | 1 669 093 | 6/2006 |
| WO | WO 98/00065 | 1/1998 |
| WO | WO 98/52473 | 11/1998 |
| WO | WO 99/52451 A | 10/1999 |
| WO | WO 00/57933 | 10/2000 |
| WO | WO 00/57933 A1 | 10/2000 |
| WO | WO 01/52751 A | 7/2001 |
| WO | WO 03/001979 A2 | 1/2003 |
| WO | WO 2004/014236 A1 | 2/2004 |
| WO | WO 2004/030520 A2 | 4/2004 |
| WO | WO 2004/030704 A2 | 4/2004 |
| WO | WO 2004/030705 A2 | 4/2004 |
| WO | WO 2004/045663 | 6/2004 |
| WO | WO 2004/066927 | 8/2004 |
| WO | WO 2006079469 | 8/2006 |
| WO | WO 2007/133103 A | 11/2007 |
| WO | WO 2008/042909 A | 4/2008 |
| WO | WO 2008/042909 A | 4/2008 |
| WO | WO 2008/107919 A | 9/2008 |
| WO | WO 2008/141034 A1 | 11/2008 |

OTHER PUBLICATIONS

International Search Report from Application EP 06 01 2688 dated Aug. 1, 2007.

JLT1204-211-229 (175): R. R. Szarmach et al., Journal of Long-Term Effects of Medical Implants, "An Innovative Surgical Suture and Needle Evaluation and Selection Program" 12(4), pp. 211-229 (2002).

George Odian, "Principles of Polymerization", III Edition, pp. 569-573 (1991).

European Search Report from application No. 07 25 4703 dated Feb. 10, 2009.

European Search Report for Appln. No. 09251035.3 dated Jun. 3, 2009.

European Search Report from application No. 07 25 4341 dated Apr. 20, 2009.

European Search Report for EP 07254341.6-1219 date of completion is Apr. 14, 2009 (3 pages).

European Search Report for Appln. No. 09250460 dated Jun. 2, 2009.

European Search Report for European Application No. 10250002.2 dated Mar. 24, 2010. (9 pages).

European Search Report for EP 10177651.6-1526 date of completion is Dec. 14, 2010 (3 pages).

European Search Report for EP 10195480.8-1219 date of completion is Apr. 27, 2011 (4 pages).

* cited by examiner

LONG TERM BIOABSORBABLE BARBED SUTURES

RELATED PATENTS

This utility application is related to U.S. patent application Ser. No. 11/673,073, the entire contents of which are incorporated herein by reference.

TECHNICAL FIELD

The present disclosure relates to biodegradable barbed sutures having degradation rates adjusted to a desired mass loss profile.

BACKGROUND OF RELATED ART

Barbed sutures, which are generally made of the same materials as conventional sutures, offer several advantages for closing wounds compared with conventional sutures. A barbed suture includes an elongated body that has one or more spaced barbs, which project from the surface of the suture body along the body length. The barbs are arranged to allow passage of the barbed suture in one direction through tissue but resist movement of the barbed suture in the opposite direction. Thus, one advantage of barbed sutures has been the provision of a non-slip attribute.

Barbed sutures are known for use in cosmetic, laparoscopic and endoscopic procedures. Using barbed sutures enables the placement of tension in tissue with less slippage of the suture in the wound. The number of suture barbs may be influenced by the size of the wound and the strength required to hold the wound closed. Like a conventional suture, a barbed suture may be inserted into tissue using a surgical needle.

Depending on the specific application, wound, and length of time needed for wound healing, there is an optimal time wherein a polymer utilized to fabricate a degradable suture has completely degraded, that is, whereupon it has lost all of its mass to the surrounding tissue. In the case of degradable sutures used in surgery, differing materials have different degradation rates, with materials having longer degradation times generally having increased tensile strength and becoming fully degraded within about 6 months. While such sutures may be suitable for use where increased tensile strength is desired, the decreased degradation time of such a suture may preclude its use for some procedures. Therefore, it may be advantageous to change the degradation profile of a material to provide a surgical suture which exhibits and maintains desired tensile properties but undergoes mass loss at a desired degradation rate.

SUMMARY

A method is provided which comprises providing a suture made from a degradable material having an elongated body with a proximal end and a distal end having barbs on its elongated body which project towards at least one end of the suture to form an included angle of less than about 90 degrees between the barbs and the elongated body and wherein the formation of barbs on the suture changes a degradation time of the suture from about 5% to about 75%.

In yet a further embodiment, a surgical suture formed from the method of the present disclosure is also provided.

BRIEF DESCRIPTION OF THE DRAWINGS

Various embodiments of the present disclosure will be described hereinbelow with reference to the figures wherein.

DETAILED DESCRIPTION

Figure 1:
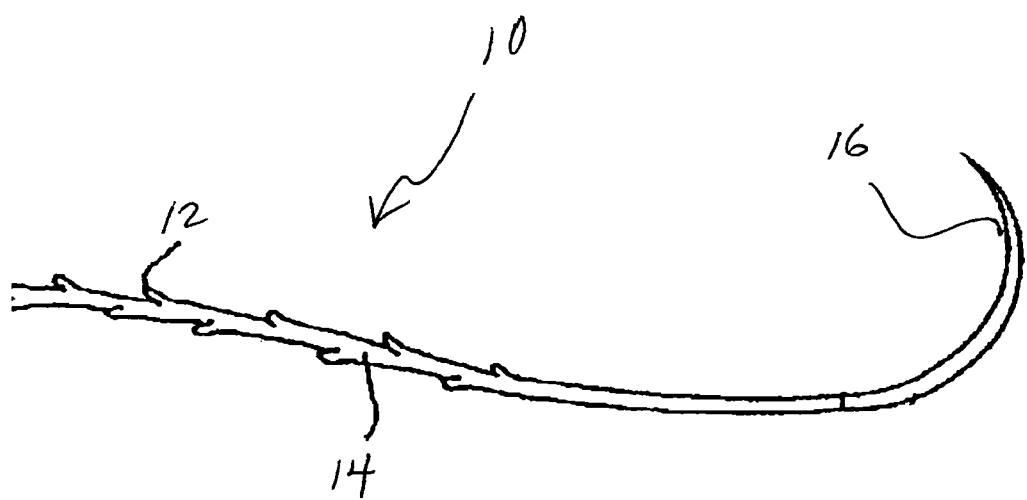
FIG. 1 is a perspective view of a barbed suture in accordance with the present disclosure attached to a needle.

Described herein is a degradable surgical suture having barbs extending from the body of the suture. The suture may have both a proximal and distal end, with barbs projecting from the elongated body towards at least one end thereby forming an included angle of less than about 90 degrees between the barbs and the suture body. The materials utilized to form the suture are selected to provide the suture with desired mass loss profile, strength retention, and tensile properties.

Moreover, a desired degradation rate may be imparted to the suture during barb formation. The machining process creates heated regions on the suture. The rate of cooling will affect polymer morphology in the localized, previously heated regions. A faster cooling rate corresponds to more amorphous regions whereas a slower cooling rate will yield less amorphous, more crystalline regions. Faster degradation rates correlate to more amorphous regions and slower degradation rates are related to more crystalline regions. Hence, increasing the number of barbs and local heated regions will have more of an effect on degradation rate.

In embodiments, amorphous regions resulting from barb formation are preserved by controlling the cooling rate of the barbed suture. For example, the suture may be exposed to a cooling fluid after barb formation. The cooling fluid may be a quench bath. Alternatively, the cooling fluid may be a cooled gas passed over the surface of the suture after barb formation. The cooling fluid may be applied within 10 minutes of barb formation, in embodiments, within 1 minute of barb formation. The temperature of the cooing fluid used will depend on the degree of crystallinity that is desired. To obtain a highly amorphous suture having the fastest absorption time, lower temperatures may be used. Increasing the temperature of the cooling fluid will increase the degradation time of the suture. The cooling fluid employed may be a cryogenic fluid, (i.e., liquid nitrogen, liquid helium, etc.) or any gas that is provided at temperatures of −100° C. to 30° C., in embodiments, −20° C. to 20° C. In embodiments, the gas employed is an inert gas. It should of course be understood that cooling fluids of different temperatures may be sequentially employed to impart the desired degree of crystallinity and thus the desired degradation rate.

In embodiments, the degradation time of the barbed suture is increased by slowing the rate at which the suture cools after barb formation to increase the degree of crystallinity. For example, the suture may be exposed to a temperature regulating fluid after barb formation. The suture may be placed in an oven to control the rate of cooling so as to increase crystallinity, thereby increasing the absorption time. Alternatively, warm gas may be passed over the surface of the suture after barb formation. As another example, the suture may be submerged in a liquid bath to control the rate of cooling, thereby providing increased crystallinity. The temperature of the temperature regulating fluid used will depend on the degree of crystallinity that is desired. To obtain a highly crystalline suture having the slowest absorption time, longer cooling times may be used by choosing temperature regulating fluids of appropriate temperature. Increasing the temperature of the temperature regulating fluid will increase the time over which the suture cools, increasing the degradation time of the suture. The temperature regulating fluid employed may advantageously be provided at temperatures of 25° C. to 200° C., in embodiments, 25° C. to 150° C. In embodiments, the gas employed is an inert gas. It should of course be understood that temperature regulating fluids of different temperatures may be sequentially employed to impart the desired degree of crystallinity and thus the desired degradation rate.

Depending, for example, on the necessary time for healing a wound, a specific rate of degradation of a suture may be desired. Since healing times vary in different organisms and different tissues, the ability to control the degradation rate of the suture may be beneficial to ensure that the suture remains intact for a long enough period of time for the wound to heal, but still absorbs within a reasonable time, typically no more than about 6 months after application of the suture to living tissue.

Any degradable material may be utilized to fashion a barbed suture of the present disclosure. Suitable degradable materials include, but are not limited to, natural collagenous materials or synthetic resins including those derived from alkylene carbonates such as trimethylene carbonate, tetramethylene carbonate, and the like, caprolactone, dioxanone, glycolic acid, lactic acid, glycolide, lactide, homopolymers thereof, copolymers thereof, and combinations thereof.

Sutures of the present disclosure may be short term degradable sutures or long term degradable sutures. The classification short term degradable sutures generally refers to surgical sutures which retain about 20 percent of their original strength at about three weeks after implantation, with the suture mass being completely degraded in the body within about 60 to about 90 days post implantation. Examples of commercially available short term degradable multifilament sutures include DEXON®, from Dexon Corporation Limited (Thailand); VICRYL® from Ethicon, Inc. (Somerville, N.J.); and POLYSORB® from United States Surgical (Norwalk, CT). The formation of barbs on a short term degradable suture may further increase the time it takes for the mass of such a suture to be completely degraded in the body after implantation.

In some embodiments, long term degradable sutures may be used to form sutures of the present disclosure. Long term degradable sutures include sutures which retain about 20 percent of their original strength at about six or more weeks after implantation, with the suture mass being completely degraded in the body within about 180 days post implantation. For example, PDS II®, a synthetic degradable monofilament suture made from polydioxanone which is commercially available from Ethicon, Inc. (Sommerville, N.J.), retains about 20 to about 30 percent of its original strength at six weeks after implantation. PDS II begins exhibiting mass loss at about 90 days after implantation, with the suture mass being completely degraded in the body about 180 days after implantation.

MAXON™ sutures, commercially available from United States Surgical (Norwalk, Conn.), are other degradable synthetic monofilament sutures which begin exhibiting mass loss at about 90 days after implantation, with the suture mass being completely degraded in the body about 180 days after implantation. MAXON sutures are prepared from a copolymer of glycolic acid and trimethylene carbonate.

Yet other sutures which may be utilized include BIOSYN™ sutures, commercially available from United States Surgical (Norwalk, Conn.). These degradable monofilament sutures are made from a terpolymer of glycolide, trimethylene carbonate, and dioxanone, are stronger than braided synthetic degradable sutures over 4 weeks post implantation, but are completely degraded between about 90 and about 110 days post implantation. Examples of specific long term degradable materials include those disclosed in U.S. Pat. No. 6,165,202, the entire disclosure of which is incorporated by reference herein.

In other embodiments, the barbed suture of the present disclosure may be made of a glycolide-trimethylene carbonate copolymer. The amount of glycolide can be from about 50% to about 90% by weight of the glycolide-trimethylene carbonate copolymer utilized to form the suture of the present disclosure, typically from about 55% to about 70% of the glycolide-trimethylene carbonate copolymer. The amount of trimethylene carbonate can thus be from about 10% to about 50% by weight of the glycolide-trimethylene carbonate copolymer utilized to form the suture of the present disclosure, typically from about 30% to about 45% of the glycolide-trimethylene carbonate copolymer.

In yet other embodiments, a suture of the present disclosure may be made of a terpolymer of glycolide, trimethylene carbonate, and dioxanone, wherein the terpolymer includes from about 56% to about 64% by weight glycolide, in embodiments from about 58% to about 62% by weight glycolide, from about 24% to about 32% by weight trimethylene carbonate, in embodiments from about 26% to about 28% by weight trimethylene carbonate, and from about 12% to about 16% by weight dioxanone, in embodiments from about 13% to about 15% by weight dioxanone.

In another embodiment, a suture of the present disclosure may be made of a lactide-glycolide copolymer wherein the copolymer includes from about 60% to about 70% by weight L-lactide, in embodiments from about 63% to about 67% by weight L-lactide, and from about 30% to about 40% by weight of glycolide, in embodiments from about 33% to about 37% by weight of glycolide.

In still another embodiment, a suture of the present disclosure may be made of a quaternary polymer of glycolide, trimethylene carbonate, caprolactone and L-lactide, wherein the polymer includes from about 62% to about 72% by weight glycolide, in embodiments from about 67% to about 71% by weight glycolide, from about 1% to about 10% by weight trimethylene carbonate, in embodiments from about 6% to about 8% by weight trimethylene carbonate, from about 12% to about 20% by weight caprolactone, in embodiments from about 15% to about 18% by weight caprolactone, and from about 1% to about 10% by weight L-lactide, in embodiments from about 6% to about 8% by weight L-lactide.

In another embodiment, a suture of the present disclosure may be made of 100% glycolide or 100% polydioxanone. In a further embodiment, a suture of the present disclosure may be made of a glycolide-L-lactide copolymer wherein the copolymer includes from about 87% to about 99% by weight glycolide, in embodiments from about 89% to about 93% by weight glycolide, and from about 4% to about 13% by weight of L-lactide, in embodiments from about 7% to about 11% by weight of L-lactide.

In a still further embodiment, a suture of the present disclosure may be made of a glycolide-epsilon caprolactone copolymer wherein the copolymer includes from about 68% to about 80% by weight glycolide, in embodiments from about 73% to about 77% by weight glycolide, and from about 20% to about 30% by weight of epsilon caprolactone, in embodiments from about 23% to about 27% by weight of epsilon caprolactone.

Sutures of the present disclosure may be of monofilament or multifilament construction. Filaments used for forming sutures of the present disclosure may be formed using any technique within the purview of those skilled in the art, such as, for example, extrusion, molding and/or solvent casting. In embodiments, the strands can be extruded through an extruder unit of a conventional type, such as those disclosed in U.S. Pat. Nos. 6,063,105; 6,203,564; and 6,235,869, the entire contents of each of which are incorporated by reference herein.

In embodiments, the suture of the present disclosure may include a yarn made of more than one filament, which may contain multiple filaments of the same or different materials. Where the sutures are made of multiple filaments, the suture can be made using any known technique such as, for example, braiding, weaving or knitting. The filaments may also be combined to produce a non-woven suture. The filaments themselves may be drawn, oriented, crinkled, twisted, commingled or air entangled to form yarns as part of the suture forming process. In one embodiment a multifilament suture of the present disclosure can be produced by braiding. The braiding can be done by any method within the purview of those skilled in the art.

Thus, utilizing the methods of the present disclosure, the mass loss profile of a barbed suture may be optimized so that the suture is completely degraded at the most appropriate time, which may be of importance in certain major surgeries such as cosmetic, laparoscopic and endoscopic procedures. For example, in embodiments, the formation of barbs on the suture may permit the use of a degradable material which normally has high tensile strength and a long period of degradation to form a suture having similar high tensile strength but a decreased degradation rate.

Barbed sutures and placement methods suitable for use according to the present disclosure include those described in U.S. Pat. Nos. 5,931,855, and 6,599,310, and U.S. patent application Publication Nos. 20030074023, 20030074023, 20040088003, 20040060409, and 20040060410, the entire disclosures of each of which are incorporated by reference herein.

Barbs may be formed on the surface of the body of a suture utilizing any method within the purview of one skilled in the art. Such methods include, but are not limited to, cutting, molding, and the like. In some embodiments, barbs may be formed by making with acute angular cuts directly into the suture body, with cut portions pushed outwardly and separated from the body of the suture. The depth of the barbs thus formed in the suture body may depend on the diameter of the suture material and the depth of the cut. In some embodiments, a suitable device for cutting a plurality of axially spaced barbs on the exterior of a suture filament may use a cutting bed, a cutting bed vise, a cutting template, and a blade assembly to perform the cutting. In operation, the cutting device has the ability to produce a plurality of axially spaced barbs in the same or random configuration and at different angles in relation to each other. Other suitable methods of cutting the barbs include the use of a laser or manual methods. The suture could also be formed by injection molding, extrusion, stamping and the like. The suture can be packaged in any number of desired pre-cut lengths and in pre-shaped curves.

In embodiments, all of the barbs may be aligned to allow the suture to move through tissue in one direction and resist moving through tissue in the opposite direction. For example, referring to FIG. 1, the barbs 12 on a suture 10 may be formed into a single directional suture. The suture 10 includes an elongated body 14 and a plurality of barbs 12 extending from the periphery of the body. The barbs 12 are yieldable toward the body of suture 10. The barbs 12 permit movement of suture 10 through tissue in the direction of movement of a needle end 16 but are generally rigid in an opposite direction and prevent movement of suture 10 in a direction opposite the direction of movement of a needle end 16.

Figure 2:
FIG. 2 is a perspective view of a bi-directional barbed suture in accordance with the present disclosure attached to a needle on each end.

In other embodiments, the barbs may be aligned on a first portion of a length of a suture to allow movement of a first end of the suture through tissue in one direction, while barbs on a second portion of the length of the suture may be aligned to allow movement of the second end of the suture in an opposite direction. For example, as depicted in FIG. 2, a suture 110 may be bi-directional. Barbed suture 110 includes an elongated body 114 having two areas, body portion 114a and body portion 114b, distal first and second needle ends 116a and 116b for penetrating tissue, and a plurality of barbs 112a and 112b extending from the periphery of the body 114. Barbs 112a on a first portion of the body 114a between the first end of suture 110 and a first axial location on the suture body permit movement of suture 110 through the tissue in a direction of movement of first needle end 116a and prevent movement of suture 110 relative to the tissue in a direction opposite the direction of movement of the first needle end 116a. Barbs 112b on second portion of body 114b between a second needle end 116b of a suture 114 and a second axial location on the body which is less than the distance from a second needle end 116b to the first axial location permit movement of a suture 114 through the tissue in a direction of movement of a second needle end 116b and prevent movement of a suture 114 relative to the tissue in a direction opposite the direction of movement of the second needle end 116b.

The barbs can be arranged in any suitable pattern, for example, in a helical pattern. The number, configuration, spacing and surface area of the barbs can vary depending upon the tissue in which the suture is used, as well as the composition and geometry of the material utilized to form the suture. Additionally, the proportions of the barbs may remain relatively constant while the overall length of the barbs and the spacing of the barbs may be determined by the tissue being connected. For example, if the suture is to be used to connect the edges of a wound in skin or tendon, the barbs may be made relatively short and more rigid to facilitate entry into this rather firm tissue. Alternatively, if the suture is intended for use in fatty tissue, which is relatively soft, the barbs may be made longer and spaced further apart to increase the ability of the suture to grip the soft tissue.

The surface area of the barbs can also vary. For example, fuller-tipped barbs can be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. Use of the combination of large and small barbs with the same suture wherein barb sizes are customized for each tissue layer will ensure maximum anchoring properties. In embodiments a single directional suture as depicted in FIG. 1 may have both large and small barbs; in other embodiments a bi-directional suture as depicted in FIG. 2 may have both large and small barbs.

Barbed sutures fabricated from a degradable material in accordance with the present disclosure maintain their structural integrity after implantation (e.g., about 80% of original strength) for a predetermined period of time, depending on the characteristics of the particular copolymer used. Such characteristics include, for example, the components of the copolymer, including both the monomers utilized to form the copolymer and any additives thereto, as well as the processing conditions (e.g., rate of copolymerization reaction, temperature for reaction, pressure, etc.), and any further treatment of the resulting copolymers, i.e., coating, sterilization, etc.

Barbed sutures of the present disclosure typically maintain their structural integrity, i.e., 80% of their original strength, after implantation for periods of time ranging approximately from about 1 day to about 50 days, in embodiments from about 3 days to about 30 days, more typically from about 5 to about 20 days.

In accordance with the present disclosure, the formation of barbs on a suture body may be utilized to change the degradation time of a suture from about 5% to about 75%, typically in embodiments from about 20% to about 60%.

A bioactive agent may be impregnated within a polymer utilized to form a suture of the present disclosure or applied to the surface thereof. In embodiments, a bioactive agent may also be included in a coating of such a suture. In some embodiments, the bioactive agent may be localized in the angle formed between the barb and the body of the suture, thereby assisting in the controlled release of the bioactive agent or agents as described in U.S. Provisional Application 60/842,763 filed Sep. 6, 2006 the entire disclosure of which is incorporated herein by reference.

Suitable bioactive agents include, for example, biocidal agents, antibiotics, antimicrobial agents, medicants, growth factors, anti-clotting agents, analgesics, anesthetics, anti-inflammatory agents, wound repair agents and the like, and combinations thereof.

Bioactive agents include substances which are beneficial to the animal and tend to promote the healing process. For example, a suture can be provided with a bioactive agent which will be deposited at the sutured site. The bioactive agent can be chosen for its antimicrobial properties, capability for promoting wound repair and/or tissue growth, or for specific indications such as thrombosis. In embodiments, combinations of such agents may be applied to a suture of the present disclosure.

The term "antimicrobial agent" as used herein includes an agent which helps the body destroy or resist pathogenic (disease-causing) microorganisms. An antimicrobial agent includes antibiotics, antiseptics, disinfectants and combinations thereof. Antimicrobial agents such as broad spectrum antibiotics (gentamicin sulfate, erythromycin or derivatized glycopeptides) which are slowly released into the tissue can be applied in this manner to aid in combating clinical and sub-clinical infections in a surgical or trauma wound site. In embodiments, suitable antimicrobial agents may be soluble in one or more solvents.

Classes of antibiotics that can be used as the antimicrobial agent include tetracyclines like minocycline; rifamycins like rifampin; macrolides like erythromycin; penicillins like nafcillin; cephalosporins like cefazolin; beta-lactam antibiotics like imipenem and aztreonam; aminoglycosides like gentamicin and TOBRAMYCIN®; chloramphenicol; sulfonamides like sulfamethoxazole; glycopeptides like vancomycin; quinolones like ciprofloxacin; fusidic acid; trimethoprim; metronidazole; clindamycin; mupirocin; polyenes like amphotericin B; azoles like fluconazole; and beta-lactam inhibitors like sulbactam.

Examples of antiseptics and disinfectants which may be utilized as the antimicrobial agent include hexachlorophene; cationic biguanides like chlorhexidine and cyclohexidine; iodine and iodophores like povidone-iodine; halo-substituted phenolic compounds like PCMX (i.e., p-chloro-m-xylenol) and triclosan (i.e., 2,4,4'-trichloro-2'hydroxy-diphenylether); furan medical preparations like nitrofurantoin and nitrofurazone; methenamine; aldehydes like glutaraldehyde and formaldehyde; and alcohols. In some useful embodiments, at least one of the antimicrobial agents may be an antiseptic such as triclosan.

To promote wound repair and/or tissue growth, one or more bioactive agents known to achieve either or both of these objectives can also be applied to the suture as wound repair agents or tissue growth agents. Such materials include any of several human growth factors (HGFs), magainin, tissue or kidney plasminogen activator to cause thrombosis, superoxide dismutase to scavenge tissue-damaging free radicals, tumor necrosis factor for cancer therapy, colony stimulating factor, interferon, interleukin-2 or other lymphokines to enhance the immune system, combinations thereof, and so forth.

Sutures in accordance with this disclosure can also include, for example, biologically acceptable plasticizers, antioxidants and colorants, which can be impregnated into the filament(s) utilized to form a suture of the present disclosure or included in a coating thereon.

As noted above, bioactive agents may be impregnated into the materials utilized to form sutures of the present disclosure or deposited on the surface thereof. Bioactive agents may be applied onto a barbed suture of the present disclosure utilizing any method within the purview of one skilled in the art including, for example, dipping, spraying, vapor deposition, brushing, and the like. In embodiments the bioactive agent, such as an antimicrobial agent, may be applied to a barbed suture of the present disclosure as part of a bioactive agent solution.

In other embodiments a barbed suture, or a portion thereof, may be coated with a biocompatible material which may impart lubricity to the suture surface, as well as further adjust the rate of degradation of a barbed suture of the present disclosure, in embodiments by decreasing the rate of degradation of the suture. The addition of a coating should not, however, adversely affect the strength and tensile properties of the suture. Suitable coatings which may be utilized are within the purview of one skilled in the art and include, for example, biodegradable coatings such as those disclosed in U.S. Patent Publication No. 20040153125, the entire disclosure of which is incorporated by reference herein.

In embodiments, mixtures useful in forming the aforementioned coatings may include a bioactive agent such as an antimicrobial agent as a predominant component in an effective antimicrobial amount. A "predominant amount" refers to one or more components which are present in an amount greater than about 50 weight percent. A "minor amount" refers to one or more components which are present in an amount up to about 50 weight percent. The minor component may include copolymers containing biodegradable monomers such as caprolactone.

An "effective antimicrobial amount" of a given component is an amount at which the component hinders the growth of bacteria to diminish or avoid contamination of the wound site.

In embodiments, the antimicrobial degradable coating composition for biocompatible surgical implantable devices is inexpensive, biocompatible, and not subject to excessive diffusion. "Biocompatible" means that no serious systemic toxicity is caused by the presence of an object in a living system. It is contemplated that biocompatible objects may cause some clinically acceptable amounts of toxicity including irritation and/or other adverse reactions in certain individuals.

In one embodiment, alkyl ester cyanoacrylates may be utilized as a coating material. Alkyl ester cyanoacrylates may be useful for medical applications because of their absorbability by living tissue and associated fluids. As described in U.S. Pat. No. 6,620,846, the entire disclosure of which is incorporated by reference herein, about 100% of a polymerized and applied cyanoacrylate may be absorbed in a period of less than 2 years, in embodiments from about 2 to about 24 months, in other embodiments from about 3 to about 18 months, and in other embodiments from about 6 to about 12 months after application. Accordingly, by coating a barbed suture with an alkyl ester cyanoacrylate, about 100% of a suture possessing a coating of polymerized and applied cyanoacrylate may be absorbed over a period of more than about two years, in embodiments from about 24 to about 48 months, in other embodiments from about 27 to about 45 months, and in other embodiments from about 30 to about 40 months after use of the suture to join tissue.

For example, alkyl ester cyanoacrylate monomers may react slowly due to relatively large pendant side groups, greatly encouraging their ability to act as a surgical adhesive. By themselves, alkyl ester cyanoacrylates are not fully curable, therefore, coating a barbed suture with alkyl ester cyanoacrylate may be useful in surgeries where a prolonged absorption rate is necessary for wound healing.

Any biodegradable polymer within the purview of those skilled in the art can be employed in the present coatings. In embodiments, the biodegradable polymer may contain epsilon-caprolactone as a component thereof. Suitable caprolactone containing copolymers include copolymers which may be synthesized by well known conventional polymerization techniques; see, for example Principles of polymerization, George Odian, III Edition; 1991 pp. 569-573, the entire contents of which are incorporated herein by reference. In some embodiments, suitable caprolactone containing copolymers are "star" copolymers obtained by polymerizing a predominant amount of epsilon-caprolactone and a minor amount of another biodegradable monomer polymerizable therewith in the presence of a polyhydric alcohol initiator.

In embodiments, the caprolactone containing copolymer may be obtained by polymerizing a predominant amount of epsilon-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

In certain embodiments, the copolymer herein can contain from about 70 to about 98, and preferably from about 80 to about 95, weight percent epsilon-caprolactone derived units, the balance of the copolymer being derived from the other copolymerizable monomer(s).

Suitable lactone monomers which can be copolymerized with epsilon-caprolactone include alkylene carbonates such as trimethylene carbonate, tetramethylene carbonate, dimethyl trimethylene carbonate; dioxanones; dioxepanones; delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-onedegradable cyclic amides; degradable cyclic ether-esters derived from crown ethers; hydroxyacids capable of esterification, including both alpha hydroxyacids (such as glycolic acid and lactic acid) and beta hydroxyacids (such as beta hydroxybutyric acid and gamma hydroxyvaleric acid); polyalkyl ethers (such as polyethylene glycol and polypropylene glycol and combinations thereof); with glycolide being a preferred monomer.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis (2-hydroxyethyl)ethylenediamine, N,N, N',N'-tetrakis (2-hydroxypropyl)ethylenediamine, dipentaerythritol, allitol, dulcitol, glucitol, altritol, iditol, sorbitol, mannitol, inositol, and the like; with mannitol being preferred.

The polyhydric alcohol initiator is generally employed in relatively small amounts, e.g., from about 0.01 to about 5, and preferably from about 0.1 to about 3, weight percent of the total monomer mixture.

The coating composition can contain from about 0.3 to about 10, and preferably from about 0.5 to about 5, weight percent of the copolymer.

Such a coating may provide sutures with the combined desirable properties of improved handling characteristics, antimicrobial activity, and an increase in resorption time.

In addition to the antimicrobial agents described above, in some embodiments the coating may include fatty acid metal salts which may impart antimicrobial characteristics to the suture.

Where the coating includes a fatty acid metal salt, the fatty acid metal salt used as the antimicrobial agent may include metal stearates. In one embodiment, the fatty acid metal salt used as the antimicrobial agent is silver stearate. In another embodiment, the fatty acid metal salt(s) used as the antimicrobial agent may be combined with fatty acid esters such as stearoyl lactylates, particularly calcium stearoyl lactylate.

Suitable fatty acids which can be used in the present coatings include the biocompatible monovalent and polyvalent metal salts of fatty acids having 6 or more carbon atoms. Examples of fatty acids useful for forming a metal salt of a fatty acid useful herein includes butyric, caproic, caprylic, capric, lauric, myristic, palmitic, palmitoleic, stearic, oleic, linoleic, linolenic, etc. Examples of monovalent metals useful for forming a metal salt of a fatty acid useful in the various embodiments described herein include lithium, rubidium, cesium, francium, copper, silver and gold. Examples of polyvalent metals useful for forming a metal salt of a fatty acid useful in the various embodiments described herein include aluminum, tin, lead, bismuth and the polyvalent transition metals. Therefore, suitable metal salts of fatty acids useful herein include fatty acid salts of lithium, rubidium, cesium, francium, copper, silver, gold, beryllium, magnesium, strontium, barium, radium, aluminum, tin, lead, bismuth, zinc, cadmium, mercury, etc.

The metal salt of a fatty acid is present in the coating composition in an effective antimicrobial amount as defined above. The metal salt of a fatty acid can consist of a single chemical compound. However, the metal salt of a fatty acid can also be a mixture of several metal salts of fatty acids. The metal salt of a fatty acid may be present in an amount from about 30 percent to about 70 percent by weight of the coating composition, in embodiments from about 45 percent to about 55 percent by weight of the coating composition.

The metal salt of a fatty acid may be relatively insoluble in cold water. When desirable, a solvent may be used to improve the working properties, e.g., viscosity, miscibility, etc., of the metal salt of a fatty acid. Suitable solvents include, for example, alcohols, e.g., methanol, ethanol, propanol, chlorinated hydrocarbons (such as methylene chloride, chloroform, 1,2-dichloro-ethane), aliphatic hydrocarbons such as hexane, heptene, ethyl acetate). When desirable, heat may be applied to the solvent mixture of metal salts of fatty acids to improve their solubility. For example, temperatures ranging from about 30° C. to about 60° C. are appropriate.

In certain embodiments, fatty acid esters may be combined with the metal salt of a fatty acid in the coating composition. Such esters include, for example, calcium stearate, stearoyl lactylate esters, palmityl lactylate esters, oleyl lactylate esters such as calcium, magnesium, aluminum, barium, or zinc stearoyl lactylate; calcium, magnesium, aluminum, barium, or zinc palmityl lactylate; calcium, magnesium, aluminum, barium, or zinc oleyl lactylate; with calcium stearate and calcium stearoyl-2-lactylate (such as the calcium stearoyl-2-lactylate commercially available under the tradename VERV from American Ingredients Co., Kansas City, Mo.) being preferred. When desirable, the fatty acid ester may be combined with a solvent. Suitable solvents include those listed above.

Where a bioactive agent is included as part of a coating, the bioactive agent and coating components may be added to separate solvents, and the resulting solvent mixtures may then be combined to form a coating solution. In other embodiments, the bioactive agent and coating components may be combined together and then mixed with solvent to form a coating solution or any combination. The order of addition is not critical and therefore may be determined through routine experimentation depending upon the desired use.

The coating can be applied to a suture by any suitable process, e.g., passing the suture through a solution of the coating mixture, past a brush or other coating solution applicator, or past one or more spray nozzles dispensing the suture coating solution. The coating solution can contain from about 30 to about 70, in embodiments from about 45 to about 55, weight percent solvent. In embodiments, a mixture of methylene chloride, hexane and ethanol may be used as a solvent. The suture wetted with the coating solution may be optionally passed through or held in a drying oven for a time and at a temperature sufficient to vaporize and drive off the solvent. If desired, the suture coating composition can optionally contain additional bioactive agents or components described above, e.g., dyes, antibiotics, antiseptics, growth factors, anti-inflammatory agents, etc.

In embodiments, sutures of the present disclosure may be dyed in order to increase the visibility of the suture in the surgical field. Any dye suitable for incorporation in sutures can be used. Such dyes include, but are not limited to, carbon black, bone black, D&C Green No. 6, and D&C Violet No. 2.

The degradation rate of the resulting sutures may be affected by several factors including the character of the coating composition and the quantity applied. In some embodiments, it may be desirable to further treat the barbed sutures of the present disclosure to obtain the desired rate of degradation. For example, in some embodiments it may be desirable to heat the sutures of the present disclosure to obtain the desired rate of degradation. The heating of the suture may also remove monomers remaining in the polymers utilized to form the sutures. Suitable temperature for heating the sutures can be from about 100° C. to about 160° C., in embodiments from about 120° C. to about 143° C., for a period of time from about 2 hours to about 24 hours, in embodiments from about 8 hours to about 16 hours. In some embodiments, the heating may take place in a vacuum.

In other embodiments, the rate of degradation of the barbed sutures of the present disclosure may be controlled by exposing them to a plasma treatment, including a low-temperature gas plasma at a pressure substantially below atmospheric for a sufficient period of time. Such methods are within the purview of those skilled in the art and include, for example, the treatment disclosed in U.S. Pat. No. 5,236,563, the entire disclosure of which is incorporated by reference herein. In embodiments, the surface treatment may be limited in time to treat the surface layer to a depth of from about 100 to about 1500 Angstroms, thereby producing a cross-linked polymer layer that will not adversely affect the desired handling qualities of the polymer.

In order to facilitate needle attachment to a suture of the present disclosure, conventional tipping agents can be applied to the braid. Two tipped ends of the suture may be desirable for attaching a needle to each end of the suture to provide a so-called double armed suture. The needle attachment can be made by any conventional method such as crimping, swaging, etc., including those described in U.S. Pat. Nos. 5,133,738; 5,226,912; and 5,569,302, the entire disclosures of which are incorporated by reference herein. Wounds may be sutured by passing the needled suture through tissue to create wound closure.

In some cases a tubular insertion device (not shown) may be utilized to introduce a barbed suture in accordance with the present disclosure into tissue. Such a tubular insertion device may have a tubular body in which the barbed suture of the present disclosure is disposed, as well as a distal end and a proximal end. In use, the pointed end of a suture of the present disclosure may be pushed with the distal end of the tubular insertion device through skin, tissue, and the like at an insertion point. The pointed end of the suture and the distal end of the tubular insertion device are pushed through the tissue until reaching an endpoint. The proximal end of the tubular insertion device is then gripped and pulled to remove the insertion device, leaving the barbed suture in place.

Where present, a tubular insertion device surrounding a barbed suture of the present disclosure protects the bioactive agent which is disposed within the barb angle formed by the barb and the suture body. Thus, the tubular insertion device may aid in keeping the barbed suture intact and the bioactive agent attached to the surface of the suture during insertion, as well as during handling, and storage of the suture. This minimizes the loss of bioactive agent to the packaging of the medical device, the environment, etc. However, upon engaging the barbed suture and tubular insertion device in vivo, moving the sheath relative to the suture to extract the sheath from the tissue exposes the bioactive agent to tissue and assists in the release of bioactive agent from the interface of the barb and the suture body into the wound closure.

Methods for repairing tissue with the sutures of the present disclosure are also provided. The sutures of the present disclosure may be utilized in any cosmetic endoscopic or laparoscopic methods. In addition, sutures of the present disclosure may be utilized to attach one tissue to another including, but not limited to, attaching tissue to a ligament.

In embodiments, sutures of the present disclosure may be held in place without the need for knots. In such cases, tissue located over a suture of the present disclosure placed in vivo may be physically manipulated or massaged into a desired position to enhance the holding of tissue in the desired position. In embodiments, the physical manipulation of tissue located over a suture of the present disclosure may enhance the release of any medicinal agent located on the suture, including any medicinal agent found in the angle between a barb and the body of a suture of the present disclosure.

For example, sutures of the present disclosure may be utilized to provide lift to tissue, which may be desirable in certain cosmetic applications. In embodiments, a procedure for closing tissue utilizing sutures includes inserting a first end of a suture, optionally attached to a needle, at an insertion point on the surface of a person's body. The first end of the suture may be pushed through soft tissue until the first end extends out of the soft tissue at an exit point. The first end of the suture may then be gripped and pulled to draw the first portion of the suture through the soft tissue so that a length of the first portion of the suture remains in the soft tissue between the point of insertion and exit point of the first end. The soft tissue may then be manually grouped and advanced along at least one portion of the suture to provide the desired amount of lift.

Specific applications of cosmetic surgeries which may utilized this physical manipulation of a suture as described above include, for example, facelifts, browlifts, thigh lifts, and breast lifts.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

What is claimed is:

1. A method comprising:
    forming barbs on an elongated body of a suture, the suture comprising a degradable material and having a crystallinity and a degradation rate,
    wherein forming the barbs alters the crystallinity of the degradable material by creating localized regions on the elongated body of the suture that change the degradation time of the suture from about 5% to about 75%.

2. The method of claim 1, wherein the suture comprises a biodegradable material selected from the group consisting of trimethylene carbonate, tetramethylene carbonate, polyanhydrides and anhydride copolymers, caprolactone, dioxanone, glycolic acid, lactic acid, glycolides, lactides, homopolymers thereof, copolymers thereof, and combinations thereof.

3. The method of claim 1, wherein the suture comprises a glycolide-trimethylene carbonate copolymer.

4. The method of claim 3, wherein glycolide comprises from about 50% to about 90% by weight of the glycolide-trimethylene carbonate copolymer and trimethylene carbonate comprises from about 10% to about 50% by weight of the glycolide-trimethylene carbonate copolymer.

5. The method of claim 1, wherein the suture comprises a quaternary polymer of glycolide, trimethylene carbonate, caprolactone and L-lactide.

6. The method of claim 5, wherein the polymer includes from about 62% to about 72% by weight glycolide, in embodiments from about 67% to about 71% by weight glycolide, from about 1% to about 10% by weight trimethylene carbonate, in embodiments from about 6% to about 8% by weight trimethylene carbonate, from about 12% to about 20% by weight caprolactone, in embodiments from about 15% to about 18% by weight caprolactone, and from about 1% to about 10% by weight L-lactide, in embodiments from about 6% to about 8% by weight L-lactide.

7. The method of claim 1, wherein the suture comprises a glycolide-dioxanone-trimethylene carbonate terpolymer.

8. The method of claim 7, wherein glycolide comprises from about 56% to about 64% by weight of the glycolide-dioxanone-trimethylene carbonate terpolymer, dioxanone comprises from about 12% to about 16% by weight of the glycolide-dioxanone-trimethylene carbonate terpolymer, and trimethylene carbonate comprises from about 24% to about 28% by weight of the glycolide-dioxanone-trimethylene carbonate terpolymer.

9. The method of claim 1, wherein the suture comprises a monofilament suture.

10. The method of claim 1, further comprising applying a coating comprising a degradable polymer on at least a portion of the suture.

11. The method of claim 10, wherein the step of applying a coating comprises applying a lactone containing copolymer.

12. The method of claim 11, wherein the lactone containing copolymer further comprises at least one monomer selected from the group consisting of alkylene carbonates, ethylene carbonate, cyclic carbonates, caprolactone, trimethylene carbonate, dioxanones, dioxepanones, delta-valerolactone, beta-butyrolactone, epsilon-decalactone, 2,5-diketomorpholine, pivalolactone, alpha, alpha-diethylpropiolactone, ethylene oxalate, 3-methyl-1,4-dioxane-2,5-dione, 3,3-diethyl-1,4-dioxan-2, 5-dione, gamma-butyrolactone, 1,4-dioxepan-2-one, 1,5-dioxepan-2-one, 1,4-dioxan-2-one, 6,8-dioxabicycloctane-7-onedegradable cyclic amides, degradable cyclic ether-esters derived from crown ethers, alpha hydroxyacids, beta hydroxyacids, polyalkyl ethers, and combinations thereof.

13. The method of claim 11, wherein the lactone containing copolymer further comprises a fatty acid metal salt.

14. The method of claim 10, wherein the coating includes a bioactive agent or drug.

15. The method of claim 14, wherein the bioactive agent comprises biocidal agents, antibiotics, antimicrobial agents, medicants, growth factors, anti-clotting agents, analgesics, anesthetics, anti-inflammatory agents, wound repair agents and the like, and combinations thereof.

16. A method comprising closing a wound with a suture of claim 1.

17. A surgical suture formed from the method of claim 1.

18. The method of claim 1, further comprising heating the localized zones of the degradable suture to a temperature from 100° C. to 160° C.

19. The method of claim 18, further comprising heating the localized zones of the degradable suture from about 2 to 24 hours.

20. The method of claim 1, further comprising exposing the barbed suture to a cooling fluid.

21. The method of claim 20, wherein exposing the barbed suture to a cooling fluid occurs within 10 minutes of barb formation.

22. The method of claim 20, wherein the cooling fluid is provided at a temperature of −100° C. to 30° C.

23. A method comprising:
    forming barbs on an elongated body of a degradable suture having a degradation time, wherein forming the barbs creates localized heated zones on the elongated body which changes the degradation time of the suture from about 5% to about 75%.

* * * * *